（12）United States Patent
Lu et al.

(10) Patent No.: US 7,553,362 B2
(45) Date of Patent: Jun. 30, 2009

(54) HIGH STRENGTH BIOLOGICAL CEMENT COMPOSITION AND USING THE SAME

(75) Inventors: Donghui Lu, Vancouver (CA); Shuxin Zhou, Vancouver (CA)

(73) Assignee: Innovative BioCeramix, Inc., Vancouver, British Columbia (CA)

(*) Notice: Subject to any disclaimer, the term of this patent is extended or adjusted under 35 U.S.C. 154(b) by 142 days.

(21) Appl. No.: 11/584,132

(22) Filed: Oct. 20, 2006

(65) Prior Publication Data
US 2007/0098811 A1   May 3, 2007

Related U.S. Application Data

(60) Provisional application No. 60/731,561, filed on Oct. 31, 2005.

(51) Int. Cl.
| A61K 6/06 | (2006.01) |
| A61L 24/02 | (2006.01) |
| C04B 12/02 | (2006.01) |
| C04B 14/00 | (2006.01) |
| C04B 14/48 | (2006.01) |
| C04B 24/00 | (2006.01) |
| C04B 28/02 | (2006.01) |
| C04B 28/34 | (2006.01) |
| C04B 7/02 | (2006.01) |

(52) U.S. Cl. .................. 106/35; 106/717; 106/781; 106/690; 106/691; 106/806; 623/23.62; 433/224; 424/602; 424/603; 424/682

(58) Field of Classification Search .................. 106/35, 106/717, 781, 690, 806, 691; 623/23.62; 433/224; 424/602, 603, 682
See application file for complete search history.

(56) References Cited

U.S. PATENT DOCUMENTS

| 3,510,322 A | * | 5/1970 | Taguchi et al. | 106/35 |
| 4,235,633 A | * | 11/1980 | Tomioka et al. | 106/35 |
| 5,415,547 A | | 5/1995 | Torabinejad et al. | |
| 5,769,638 A | | 6/1998 | Torabinejad et al. | |
| 5,811,302 A | | 9/1998 | Ducheyne et al. | |
| 6,518,212 B1 | * | 2/2003 | Wagh et al. | 501/111 |
| 7,083,672 B2 | * | 8/2006 | Wagh et al. | 106/35 |

(Continued)

FOREIGN PATENT DOCUMENTS

JP         11292600         10/1999

OTHER PUBLICATIONS

Fridland, M. et al., MTA solubility: A long term study, JOE 31:5, pp. 376-379 (May 2005).

(Continued)

*Primary Examiner*—C. Melissa Koslow
(74) *Attorney, Agent, or Firm*—Todd N. Hathaway

(57) ABSTRACT

A hydraulic cement for biomedical applications. The cement sets in-situ, hardening when exposed to water to produce nano-dispersed composite of calcium-silicate-hydrate gel mixed with hydroxyapatite. In comparison with prior cements, the composition provides high biocompatibility, high bioactivity and high biomechanical strength, due to the composite structure of the calcium silicate hydrate reinforced with co-precipitated particles of hydroxyapatite. Biocompatibility is also increased due to an absence of aluminum and magnesium in the composition. The cement is suitable for variety of applications, including dental implants, bone fixation, and bone repair.

18 Claims, 6 Drawing Sheets

U.S. PATENT DOCUMENTS

2003/0003160 A1    1/2003    Pugh et al.
2003/0159618 A1    8/2003    Primus
2006/0078590 A1*    4/2006    Hermansson et al. ....... 424/426

OTHER PUBLICATIONS

Mitchell, P. et al., Osteoblast biocompatibility of mineral trioxide aggreagate, Biomaterials 20, pp. 167-173 (1999).

Diarra, M. et al., Elaboration and evaluation of an intraoral controlled release dilvering system, Biomaterials, 19, pp. 1523-1527 (1998).

Persson, B., Seven-year study on the effect of silica fume in concrete, Elsevier, pp. 139-155 (1998).

Oonishi, H. et al., Particulate bioglass compared with hydroxyapatite as a bone graft substitute, Clinical Orthopaedics and Related Research, 334, pp. 316-325 (1997).

Hamanishi, C., et al., Self-setting, bioactive, and biodegradable TTCP-DCPD apatite cement, J. of Biomedical Materials Research, 32, pp. 383-389 (1996).

Torabinejad, M. et al., Physical and chemical properties of new root-end filling material, J. of Endodontics, 21:7, pp. 349-353 (1995).

Driessens, F. et al., Formulation and setting times of some calcium orthophosphate cements: A pilot study, J. of Materials Science: Material in Medicine, 4, pp. 503-508 (1993).

Mindess, S. et al., Concrete, Civil engineering and engineering mechanics series, pp. 76-111 (1981).

* cited by examiner

HIGH STRENGTH BIOLOGICAL CEMENT COMPOSITION AND USING THE SAME

RELATED CASES

This application claims the priority of Provisional Patent Application Ser. No. 60/731,561, filed Oct. 31, 2005.

BACKGROUND OF THE INVENTION a. Field of the Invention

The present invention relates generally to hydraulic cements for medical and dental applications, and, more particularly, to an aluminum-and magnesium-free hydraulic cement that produces a nano-dispersed composite of calcium-silicate-hydrate gel mixed with hydroxyapatite, that exhibits good mechanical strength and high biocompatibility and bioactivity.

b. Related Art

Hydraulic cements are commonly utilized in construction and also in medical and dental applications.

One of the most important hydraulic cements is calcium di-silicate and tri-silicate-based cement, which is widely used in construction. There are three main compounds in the cement: dicalcium silicate (C2S), tricalcium silicate (C3S), and calcium aluminate (C3A). Highly crystalline calcium hydroxide ($Ca(OH)_2$) (referred to later as CH) and amorphous calcium-silicate-hydrate (C—S—H) are the principal phases that form in the hydration process of C2S and C3S. The hydrated cement paste consists of approximately 70% C—S—H and 20% CH, with additional phases including about 7% sulfoaluminate, and about 3% of secondary phases. The calcium hydroxide component, which is formed as a result of the setting reaction, negatively effects the quality of the set cement, since CH is soluble in water and has low strength.

Certain Portland cement—based materials (referred to as mineral trioxide aggregate, or MTA) have been used for medical and dental applications, such as endodontic dental treatment and the retention of cores [Vargas et al., "*A Comparison of the In vitro Retentive Strength of Glass-Ionomer Cement, Zinc-Phosphate Cement, and Mineral Trioxide Aggregate for the Retention of Prefabricated Posts in Bovine Incisors*" *J. Endodont.* 30(11) 2004, 775-777]. MTA, like Portland cement, consists primarily of tricalcium silicate, tricalcium oxide, and tricalcium aluminates. [Torabinejad et al. "*Physical and chemical properties of a new root-end filling material*". *J Endodont* 21(1995) 349-253]. The hydration product of calcium aluminates is a mixture of calcium-aluminate compounds and calcium-sulfate-aluminate compounds [Concrete, J. F. Young, pp76-98, Prentice-Hall, Inc, Englewood Cliffs, 1981].

MTA, has been used in many surgical and non-surgical applications, and possesses the biocompatibility and sealing abilities requisite for a perforation material [Lee, et al, "*Sealing ability of a mineral trioxide aggregate for repair of lateral root perforations*" *J Endod* 1993; 19:541-4.]. It can be used both as a non-absorbable barrier and restorative material for repairing root perforations. Because it is a hydrophilic cement and requires moisture to set, MTA has been the barrier of choice when there is potential for moisture contamination, or when there are restrictions in technical access and visibility during the restorative process. MTA also has good compressive strength after setting.

In one example, Torabinejad et al (U.S. Pat. Nos. 5,415,547, and 5,769,638) disclosed an improved method for filling and sealing tooth cavities which involved the use of an MTA cement composition, including the ability to set in an aqueous environment. The cement composition comprises Portland cement, or variations on Portland cement, which exhibits physical attributes sufficient to form an effective seal against re-entrance of infectious organisms. However, the MTA composition derived from Portland cement is gray in color, which is unsuitable for many dental applications. Moreover, among other problems, MTA contains significant amounts of aluminum and consequently presents certain biocompatibility and toxicity concerns, as will be discussed below.

Primus (U.S. Pat Appl. 20030159618) disclosed a process for making a white, substantially non-iron containing dental material formed from Portland cement. The material, also referred to as White MTA or WMTA, may be used as a dental cement, dental restorative or the like. However, this process only decreases the iron content and does not improve the biological properties of the material, since it still contains aluminum.

A number of investigators have reported improvement of mechanical strength of Portland cement by adding silica fume ($SiO_2$, referred later as S) in order to decrease $Ca(OH)_2$ content in the hydrated cement [Mitchell, Et Al, "*Interaction Of Silica Fume With Calcium Hydroxide Solutions And Hydrated Cement Pastes*", *Cement And Concrete Research* (1998), 28(11), 1571-1584 And Persson "*Seven-Year Study On The Effect Of Silica Fume In Concrete*" *Advanced Cement Based Materials* (1998), 7(3/4), 139-155]. The mechanism depends on the silica fume reacting with the calcium hydroxide CH to produce an amorphous C—S—H gel having a high density and low Ca/Si ratio. This demonstrates that removal of CH can make for substantial improvement of the set cement.

The foregoing effect was also recognized in Japanese patent no. JP 11-292600 "*Production of slightly calcium leaching cement composition.*" (Oct. 26, 1999). The patent disclosed a "slightly calcium leaching Portland cement composition" with a phosphate or fluorides added to the cement material (e.g. Portland cement). The resulting product is a cement hydrate with reduced production in calcium hydroxide and an increase of calcium phosphate compounds, e.g. hydroxyapatite. The material is designated for treatment of hazardous wastes, such as nuclear waste, to prevent leaching, and also for construction materials and structural materials, which would include relatively high levels of impurities and consequently exhibit toxicity unsuitable for medical/dental use. Moreover, when Portland cement is combined with "phosphoric acid compounds" or fluorides, aluminum phosphate or aluminum fluoride result. Aluminum compounds are therefore present in this material as well, similar to the situation with MTA.

The presence of aluminum is a major disadvantage of the materials derived from Portland cement (such as MTA or WMTA) when used for biomedical and dental applications. Aluminum ions will be released into human biological system during hydration and setting reaction of such cement. Moreover, in the case of permanent and long term applications, such as dental filling, bone implants, and use in orthopedic surgery, the calcium sulfate aluminates in the cements will continually release aluminum ions into the human biological system [Fridland, et al., "*MTA Solubility: A Long Term Study*", JOE—Volume 31, Number 5, May 2005, and *JOURNAL OF ENDODONTICS*, VOL. 29, NO. 12, DECEMBER 2003].

Research indicates that aluminum ions are toxic to the human biological system. For example, aluminum inhibits mineralization of bone, and is toxic to osteoblasts. Diseases that have been associated with aluminum include dialysis dementia, renal osteodystrophy and Alzheimer's disease. Aluminum also has adverse effect on red blood cells, parathyroid glands and chromosomes. Accumulation of aluminium in the body tends to occur when the gastrointestinal barrier is circumvented, as is the case with implants or dental treatments. See for example, Monteagudo, et al., "*Recent developments in aluminum toxicology*", *Medical toxicology and adverse drug experience* (1989 January-February), 4(1), 1-16. Ref: 158; Rodriguez, et al., "*Aluminum administration in the rat separately affects the osteoblast and bone mineralization*", *J Bone Miner Res* 1990 January;5(1):59-67; SAVARINO. et al., "*In vitro investigation of aluminum and Fluoride release from compomers, conventional and resin-modi. Ed glass-ionomer cements: A standardized approach*," *J. Biomater. Sci. Polymer Edn, Vol.* 11, No. 3, pp. 289-300 (2000). One commonly observed result of the awareness of aluminum toxicity to human bodies is the gradual elimination of aluminum cooking utensils from general (and in particular household) use, and their replacement by stainless steel utensils; this process continues despite the fact that aluminum utensils provide excellent heat transfer characteristics due to high thermal conductivity (up to 300 W/mK), as opposed to the relatively low thermal conductivity (and significantly higher cost) of stainless steel.

All of the prior cement compositions discussed above are based on (or derived from) Portland cement, and as such rely on aluminum compounds to achieve early strength when setting. If the aluminum were to be removed from such compositions, the strength increase would be much slower, rendering the cement useless for its intended applications. As will be described below, the hydraulic cement of the present invention does not use aluminum, and instead, employs inventive materials science (e.g., inclusion of kinetics-accelerating phosphate compounds) and processing methods (e.g., controlled particle size) to achieve early setting strength without aluminum compounds.

There are instances reported in the literature where phosphates have been combined with calcium-silicate Portland-type cements. For example Ma et al ["*Effect of phosphate additions on the hydration of Portland cement*" Advances in Cement Research (1994), 6(21), 1-12] discussed the effect of phosphate additions on the hydration process of Portland cement. The phosphate-modified cements, which were not designed for biomedical applications, produced more hydration heat and exhibited faster hydration rates than the reference ordinary Portland cement. The reaction products were amorphous, but hydrothermal treatment at 160° C. of ordinary Portland cement (OPC) modified by $CaHPO_4$ allowed transformation of a poorly crystalline phosphate phase into hydroxyapatite, resulting in improved flexural strengths. A number of disadvantages limit the applications of the process, such as the need for hydrothermal treatment for formation of the hydroxyapatite, and the need for high pressure (28 MPa) pressing in order to achieve an adequately high strength. Also, the process described by Ma et al can not be used for forming a uniform composite structure, and the mechanical strength was not significantly improved by comparison with Ordinary Portland cement (OPC). Moreover, the cements still relied on aluminum compounds to gain early strength. Recently, U.S. Pat. No. 7,083,672 (Wagh et al) disclosed phosphosilicate ceramics comprising 65-85 weight percent of a powder and about 15-35 weight percent of a liquid, which are combined to form a paste for various uses, for example, as a bone cement for dental and orthopedic purposes. The powder component comprises a "sparsely soluble oxide" powder, such as magnesium oxide powder, monovalent alkali metal phosphate powder and a sparsely soluble silicate powder (e.g. $CaSiO_3$). The liquid component comprises a pH modifying acid (e.g. $Ca(H_2PO_4)_2H_2O$), such that pH is in the range of 3-7 (preferably nearly 3) during setting of the cement. Hydroxyapatite (HAP) powder may be introduced into the composition by admixing an HAP powder into the other powder; there is no provision for reactive, in-situ formation of HAP, which limits the possibilities of composite formation, and also provides less than satisfactory mechanical properties and bioactivity/biocompatibility in the set material.

Chemically bonded ceramics (CBC) in the system CaO—$SiO_2$—$P_2O_5$—$H_2O$ were investigated by Hu et al ["*Investigation of hydration phases in the system* CaO—$SiO_2$—$P_2O_5$—$H_2O$" J. Mater. Res. 1988, 3(4) 772-78] and Sterinke et al [*Development of chemically bonded ceramics in the system* CaO—$SiO_2$—$P_2O_5$—$H_2O$" Cement and Concrete Res. 1991 (21)66-72]. The powders of CBC were synthesized by sol-gel process and then fired at a temperature of 700-1000 C for 2 hours. The components of the powders before hydration are calcium hydroxyapatite (major), di-calcium silicate, γ-2CaO—$SiO_2$, amorphous calcium silicate, and amorphous calcium phosphate [Hu, et al, "*Studies of strength mechanism in newly developed chemically bonded ceramics in the system* CaO—$SiO_2$—$P_2O_5$—$H_2O$" Cement and Concrete Res. 1988 (18)103-108]. However, the mechanical properties were not improved when the samples were hydrated at room temperature. In order to increase the mechanical strength of CBC, the samples were made with high pressure formation (345 MPa) and were subsequently hydrated at high temperatures.

Calcium phosphate cement (CPC) was first reported in a binary system containing tetracalcium phosphate (TTCP) and dicalcium phosphate anhydrate (DCPA) [L. C. *Chow* et al. *J. Dent Res.*, 63, 200, 1984]. The advantages of CPC include self-setting (similar to OPC), plus an apatitic phase in the set cement (e.g. HAP, or other similar phases of varying chemistry and crystallinity). Consequently, CPC is a bioactive material that interract with body fluids through a dissolution-reprecipitation process. This has led to applications such as bone replacement and reconstruction, and also drug delivery [M Dairra, et al. *Biomaterials,* 19 1523-1527, 1998; M. Otsuka, et al. *J. of Controlled Release* 43(1997)115-122, 1997, Y. Tabata, *PSTT*, Vol. 3, No. 3, 80-89, 2000; M. Otsuka, et al. *J. of Pharm. Sci.* Vol. 83, No. 5, 1994].

Calcium phosphate cement (CPC) is typically formulated as a mixture of solid and liquid components in pertinent proportions, which react to form the apatite. The physicochemical reactions that occur upon mixing of the solid and liquid components are complex, but dissolution and precipitation are the primary mechanisms responsible for the final apatite formation [C. Hamanish et al *J. Biomed. Mat. Res.*, Vol. 32, 383-389, 1996; E. Ferandez et al *J. Mater. Sci. Med.* 10, 1999]. The reaction pathway in most CPC systems does not lead to stoichiometric HAP, but rather to calcium-deficient $Ca_{10-x}(HPO_4)_x(PO_4)_{6-x}(OH)_{2-x}$, similar to that found in bone. The process parameters, such as Ca/P ratio, powder/liquid ratio, seeds concentration type, and nature of reagents, control the final properties, such as phase content, porosity, strength, setting time, phase transformation kinetics, and microstructure of the CPC-derived hydroxyapatite (CPC-HAP). Synthetic CPC may also incorporate carbon-containing phases, similar to bone minerals.

Bermudez et al [*J. Mat. Sci. Med.* 4, 503-508, 1993; ibid 5, 67-71, 1994] correlated the compressive strength of CPC to the starting Ca/P ratio in systems of monocalcium phosphate monohydrate (MCPM) and calcium oxide. The major drawback of CPC technology is low mechanical strength (generally below 20 MPa compressive), which severely limits its suitability for medical/dental materials and devices. Intensive research continues on increasing strength of CPC, for example sophisticated processing methods involving reduction or elimination of flaws (such as voids or cracks) from set cement have been reported [T Troczynski, "*Bioceramics-A Concrete Solution*", *Nature Materials*, [3] 13-14, January 2004]. As CPC behaves as a typical brittle, flaw-sensitive ceramic, reduction of flaws translates to increased strength. However, substantial elimination of flaws in CPC setting in contact with living tissue such as bone or dentine may be impractical or impossible. In some situations it is also not desirable, as hard tissue such as bone may integrate easier with porous CPC as compared to dense CPC. There is constantly a continuing need to be able to increase strength of biological cements without substantial modification of their porosity or flaws density.

A combination of the oxides of calcium, phosphorous and silicon (with the major component being silica, in an amount of about 45 wt %) results in a bioactive glass material, providing excellent in-vivo performance and stimulation of cell growth, sometimes even better than hydroxyapatite or other calcium phosphates [e.g. Oonishi et al, "*Particulate Bioglass compared with hydroxyapatite as a bone graft substitute*", *J. Clin. Orthop. Rel. Res.* 334, 316-25, 1997; also U.S. Pat. No. 5,811,302 by Ducheyne et al, Sep. 22, 1988]. This is an indication that the biomaterials synthesized through combination of the three oxides of calcium, phosphorous and silicon may become even more bioactive than calcium phosphates that lack silica. This observation has been explored by partial replacement of Ca by Si in the solid solution through high-temperature treatment and sintering [e.g. compare US Pat. Appl. 20030003160, Jan. 2, 2003, S. M. Pugh et al, "Synthetic biomaterial compound of calcium phosphate phases particularly adapted for supporting bone cell activity"]. Unfortunately, although chemically advantageous, bio-glass must be processed at very high temperatures (generally in excess of 1000 C), and is a rather dense, weak and brittle material. Another disadvantage of bio-glass is that it does not easily dissolve in biological environments (due to dense $SiO_2$ film coverage), which is desirable in some applications, e.g. for stimulation of bone growth.

The literature has recently reported attempts to address these issues, by combining the three oxides of calcium, phosphorous and silicon into porous crystalline composite material, which would possess a high bioactivity similar to the bio-glass, but which would be stronger (even though porous) and easier to resorb in-vivo [A. R. El-Ghannam, "*Advanced bioceramics composite for bone tissue engineering: design principles and structure-bioactivity relationship*", *J. Biomed. Mater. Res.* 69A, 490-501, 2004]. The precursors to the three oxides (plus sodium oxide) were heat treated at high temperatures (130-800 C) to result in a porous composite of crystalline silica (quartz or crystobalite), and variety of calcium-phosphates or calcium-sodium-phosphates. Excellent bioactivity of these composites was demonstrated. Unfortunately the need for the high temperature treatment makes this composite material difficult to apply as biomaterial, as all the processing and shaping operations must take place outside of the application site.

The advantages of the simultaneous presence of Ca, P, and Si elements in bioceramic materials has been also recognized through sinter-processing (high temperature heat treatment) of silicon substituted hydroxyapatite and other calcium phosphates [Alexis M Pietak, Joel W. Reid, Michael Sayer, "*Electron spin resonance in silicon substituted apatite and tricalcium phosphate*", Biomaterials, June 2005, p3-14; Joel W. Reid, Loughlin Tuck, Michael Sayer, Karen Fargo and Jason A. Hendry, "*Synthesis and characterization of single-phase silicon-substituted α-tricalcium phosphate*," Biomaterials, Volume 27, Issue 15, May 2006, Pages 2916-2925]. The need for high-temperature processing of the biomaterials is a drawback of this approach as well, similar to the bioglass described above.

The bioglass, calcium phosphates, and all cements in the CPC family of cement, are unstable in biological environments, and eventually dissolve, frequently providing room and a chemical environment encouraging growth of new tissue, such as bone tissue. However, in many applications, such as endodontics or orthopedic applications where the cement must have sufficient strength at all times, resorption is not desirable. The present invention is directed to non-resorbable biological cements that are based on calcium silicates.

Accordingly, there exists a need for a hydraulic cement for use in medical and dental applications that is free from aluminum and other elements/compounds which present potential toxicity problems in a biological system. Still further, there exists a need for such a hydraulic cement that is bio-compatible with the surrounding tissue and system in additional respects, and that exhibits a high degree of bioactivity. Furthermore, there exists a need for such a hydraulic cement which can set and gain sufficient strength at room or near-room temperatures (such as body temperature). Still further, there exists a need for such a hydraulic cement which, when set, will exhibit substantially no resorption during lifetime of the implant Still further, there exists a need for such a hydraulic cement that develops sufficiently high strength, stability and resistance to fracture/brakage to be suitable for use as a bone substitute, in dental work, in orthopedic surgery, and in other medical and dental applications. Still further, there exists a need for such a hydraulic cement that can be placed and set under temperatures, pH levels and other conditions that are compatible with the human biological system.

SUMMARY OF THE INVENTION

The present invention provides a new composition of hydraulic cement, and methods for making and using the composition for biomedical and dental applications. The new hydraulic cement has high mechanical strength, high bioactivity, and high biocompatibility. The cement is resistant to corrosion and is stable and durable in variety of environments, including biological environments. The cement sets at room or near-room temperatures and does not resorb (dissolve) in a biological environment.

The cement of the present invention is an aluminum-free and magnesium-free phospho-silicate hydraulic cement. The cement comprises oxides of calcium, phosphorous and silicon, and excludes magnesium and aluminum in any form. Although free of magnesium and aluminum compounds, the new cement rapidly gains strength through hydration-assisted setting at room temperature and pressure. As a result, it has high early strengths, high overall compressive strength, adjustable setting times, low hydration heat, and resistance to chemical degradation.

The cement compositions comprise at least one phosphate compound and at least one calcium silicate compound. The cement of present invention preferably uses synthetic (high purity) di- and tri-calcium silicates ([$2CaO.SiO_2$], [$3CaO.SiO_2$]), with no aluminum. The additive powders are preferably calcium phosphates, including dicalcium phosphate or monocalcium phosphate.

In a preferred embodiment, the first of the principal components of the biocement is calcium oxide (CaO), in the range of about 45%-80% by weight of cement in the composition, preferably in the range of about 50 wt %-70 wt %. The second of the main components is silica ($SiO_2$), in the range of about 10%-35% by weight of cement in the composition, preferably in the range of about 15 wt %-30 wt %. The calcium oxide and silica are preferably provided in combined form, as di-calcium and/or tri-calcium silicates. The third of the main components is the phosphate (preferably in the form of $P_2O_5$ or as alternative ionic form), in range of about 1%-30% by weight of cement in the composition, preferably in the range of about 3 wt %-15 wt %.

Complex chemical and physical reactions and processes take place after the hydraulic cement powder components are mixed with water, which is preferably substantially pure water. These reactions involve hydration of calcium silicate compounds and dissolution of phosphate compounds, and the precipitation of calcium phosphates, including hydroxyapatite. These reactions proceed in an alkaline environment of pH>10. The dissolution of the phosphate compounds and precipitation of calcium phosphates take place during the hydration of the calcium silicate compounds, so that the by-products of the hydration of the calcium silicate compounds, particularly calcium hydroxide, are taken up and utilized to precipitate calcium phosphate compounds. More specifically the calcium silicate compounds (mainly di-calcium silicate (C2S) and tri-calcium silicate (C3S) react with water to produce calcium silicate hydro-gel and calcium hydroxide (CH). The inorganic chemical phosphate compound reacts in-situ with the calcium hydroxide to form a high strength hydroxyapatite precipitate, which is dispersed throughout the Calcium-Silicate-Hydrate (C—S—H) matrix, therefore simultaneously removing the CH (which as noted above, is ordinarily a structurally weak component in the body of set cement).

As a result, the biocement of the present invention has enhanced functionality, in particular enhanced strength and corrosion and dissolution resistance due to the absence of CH, combined with enhanced biocompatibility and bioactivity due to the presence of HAP and/or other phosphate inclusions. The HAP inclusions produced reactively in-situ also contribute substantially to the overall compressive strength of the set cement, both directly (through bonding to the C—S—H structure) and indirectly (through removal of the structurally weak CH inclusions). Additionally, HAP is much more resistant to environmental effects than CH, rendering the CPSC of the present invention more resistant to corrosion.

Silicate nanoparticles may optionally be introduced into the cement composition of the present invention to improve mechanical, setting, and biological properties. The silicate nanoparticles may suitably be in a colloidal silica solution that is mixed with the biocement powder. Silicate nanoparticles can be mixed with the biocement powder by ball milling. The colloidal nanoparticle will speed up the hydration of calcium silicate compounds and increase mechanical strength. Also, the silicate can enhance biocompatibility and bioactivity of biocement.

Furthermore, for dental applications, radio-opaque materials may be added to the composition to enhance absorption of X-rays, for improved visibility of the cement under X-ray examination. Examples of radio-opaque materials suitable for dental applications include, but are not limited to, barium sulfate, zirconium oxide, bismuth oxide, tantalum oxide, and mixtures thereof. Radio-opacity is very desirable in the cases of dental fillings and sealings; for some applications, however, it is not necessary to have high radio-opacity, for instance, pulp capping or in many orthopedic applications.

The novel biocement of the present invention may also be used as a bioactive coating for medical devices and drug delivery vehicles. The cement coating can be deposited on the surface of a medical device at room temperature, which is advantageous by comparison with coating techniques that require elevated temperatures for deposition. Single or multiple drugs can be encapsulated into the biocement matrix using an in-situ process. A variety of coating deposition technologies, well known in the art, may be used for deposition of films of the biocement on substrates such as implants; the techniques may include, without limitation, dip-coating, spray-coating, electro-assisted coating, aerosol-coating, and combinations thereof.

Figure 1:
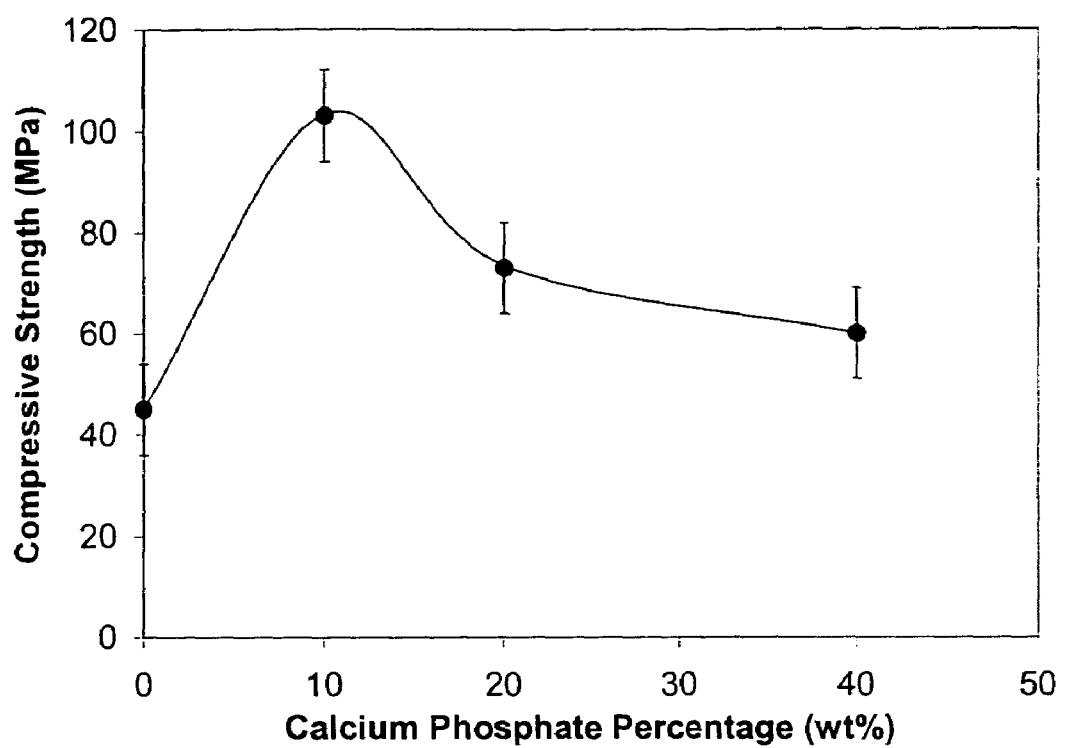
FIG. 1 is a graph illustrating compressive strength of the set hydraulic cement of the present invention, as a function of calcium phosphate content.

DETAILED DESCRIPTION OF THE INVENTION a. Overview

The present invention provides novel cement compositions and methods of making them and using them in a variety of medical and dental applications. The hydraulic cement (called later BA) of the present invention has high mechanical strength, adjustable setting time, low hydration heat, resistance to degradation, high bioactivity and biocompatibility, and stability in corrosive environments.

The hydraulic cement of the present invention is obtained through a novel chemical process of in-situ formation of hydroxyapatite/calcium silicate hydrate gel composite, at room- or near-room-temperature and pressure, accompanied by the removal of CH during cement hydration, resulting in aluminum-free and magnesium-free hydraulic phosphor-silicate cement. This is accomplished by reacting the CH in-situ with phosphate ions to precipitate much stronger and chemically resistant calcium phosphate, in particular hydroxyapatite (HAP), intimately mixed with the C—S—H gel. The composite cement has high mechanical strength, as well as biocompatibility, bioactivity, and adjustable setting times. These properties do not require application of hydrothermal treatment, pressure-assisted forming, or high temperature sintering of the components. The setting time is adjusted through provision of micron-size particles of the hydrating powders, thus removing the need for early-hydration chemicals containing aluminum.

The major components of the biocement compositions, which make up approximately 60% by weight of cement in the cement composition, comprise at least one calcium silicate compound and at least one phosphate compound. Suitable calcium silicate compounds include, but are not limited to, dicalcium silicate C2S ($2CaO.SiO_2$), tetracalcium silicate C4S ($4CaO.SiO_2$), tricalcium silicate C3S ($3CaO.SiO_2$) and mixtures thereof. Suitable phosphate compounds include, but are not limited to, calcium phosphates, with calcium phosphate monobasic generally being preferred. The phosphates may contain hydration water. More complex (pre-reacted) phosphates may also be used, such as many variants of the calcium phosphates. The at least one phosphate compound is preferably included in an amount sufficient to react a major portion of the calcium hydroxide that is produced by hydration of the calcium silicate compound or compounds. Other calcium compounds may be included in the cement composition, including but not limited to, calcium oxide, calcium carbonates, calcium hydroxides, and mixtures thereof. The at least one calcium silicate compound is suitably included in an amount in the range from about 30% to about 99% by weight of the cement composition, preferably in the range from about 40% to about 80%. The at least one phosphate compound is suitably included in an amount in the range from about 1% to about 70% by weight of the cement composition, preferably in the range from about 5% to about 30%. Where present, ancillary compounds are preferably included in a total amount less than about 30% by weight of the cement composition.

A significant difference from prior art cements is that the hydraulic cement of the present invention is in its preferred embodiment both magnesium-free and aluminum free, or at least substantially free of such materials, and still maintains desirable setting and set cement characteristics. By contrast, as discussed above, all Portland cement derived hydraulic cements require fast hydrating aluminum compounds such as calcium aluminates, to achieve a sufficiently high rate for the initial hydration reaction and strength buildup of the setting cement, but with negative consequence for biocompatibility.

Minor compounds that may be included in the cement compositions in present invention include, but are not limited to, calcium oxide, silicon dioxide, iron oxide, other metal oxide compound, calcium sulfate, calcium sulfate dihydrate ($CaSO_4.2H_2O$), and mixtures thereof. The minor compounds will generally make up less than 10% by weight of cement in the composition and preferably no more than 30% by weight.

For some dental applications, radio-opacity materials may be added to the biocement composition for improving absorption of X-rays. Suitable radio opacity materials may be selected from heavy metals, oxides of heavy metals and salts of heavy metals, and may include, but are not limited to, gold, silver, barium bismuth, tantalum, barium sulfate, zirconium oxide, bismuth oxide, tantalum oxide, and mixtures thereof. The radio-opaque materials will generally constitute less than 70% by weight of cement in the composition; suitably, the radiopaque substance or substances may be included in an amount in the range from about 3% to about 50% by weight of the cement composition, preferably in the range from about 10% to about 40%.

When water is mixed with the novel cement, a complicated set of reactions is initiated. The phosphate and calcium compounds quickly dissolve in water and precipitate to produce new calcium phosphate compounds, especially hydroxyapatite, when pH is above 7.0. The reaction speed is adjustable in range from 20 min to 2 days to meet to the requirements of applications, through minor change in the system chemistry and precursor morphology.

Initially, the calcium silicates react with the water to produce a calcium silicate hydrate gel ($CaO$—$SiO_2$—$H_2O$ gel); however, the rate of hydration reaction of calcium silicates is slower than that of the formation of hydroxyapatite and calcium phosphates. Consequently, in the process of co-precipitating nano-size particles of calcium silicate hydrate gel fill the voids among the precipitating hydroxyapatite particles.

A key aspect of the present invention is the in-situ formation of a hydroxyapatite/calcium silicate hydrate gel composite at room temperaturse, in ordinary prepared cement paste, without a need for elevate pressures or temperatures, and in particular without a need for thermal treatment of the setting cement paste, and without a need for Al or Mg ions participating in the reaction. The formation of the C—S—H/HAP composite is accompanied by a decrease of CH content in the set cement. The resulting composite biocement material, due to its decreased CH content, provides significantly increased mechanical strength, with the calcium phosphate and hydroxyapatite acting as a reinforcement phase and calcium silicate hydrate gel forming the matrix of the composite structure.

An important aspect of the current invention is its aluminum-free composition, which provides significantly improved biocompatibility, bioactivity and safety with as compound prior cements. As noted above, soluble aluminum is highly toxic to the osteoblast and inhibits mineralization of bone, may cause dialysis dementia, renal osteodystrophy and Alzheimer's disease.

By comparison with the cement disclosed by Wagh (as discussed above), the main components of the cement of the present invention are di-calcium and tri-calcium silicates and phosphate; the cement does not include magnesium oxide. Also, mono-calcium silicate (e.g. $CaSiO_3$) powders are not necessary in the present invention, and it is not necessary to have any "sparsely soluble oxide" powder for the setting and hardening reactions. The liquid used to hydrate (set) the cement of the present invention is substantially neutral (pure) water, without any acidic pH modifying agents being needed for the cement setting and hardening reactions; to the contrary, the pH conditions during setting in present invention are alkaline, typically above pH=10. Moreover, the hydroxyapatite in present invention is produced through in-situ chemical reaction of the phosphate powder and the calcium hydroxide that is produced by the hydration of the calcium silicates, thus introducing nano-size HAP into the composition and thereby enhancing the mechanical properties and biocompatibility and bioactivity of the set cement; these reactions do not take place in Wagh's composition.

b. Reactions and Materials

The precipitation reaction (A) of calcium phosphate apatite is as follows:

$$10Ca^{2+} + 6PO_4^{3-} + 2OH^- \rightarrow Ca_{10}(PO_4)_6(OH)_2 \quad (A)$$

where the Ca/P ratio is between 1.2 and 2.0.

The hydration reactions (B, C) of calcium silicates can be approximated as follows:

$$2[3CaO.SiO_2] + 6H_2O \rightarrow 3CaO.2SiO_2.3H_2O + 3Ca(OH)_2 \quad (B)$$

$$2[2CaO.SiO_2] + 4H_2O.3CaO.2SiO_2.3H_2O + Ca(OH)_2 \quad (C)$$

where the calcium hydroxide CH is the hydration product which contributes to the high alkalinity of the cement. The calcium silicate hydrate is not a well-defined compound and the formula of ($3CaO.2SiO_2.3H_2O$) is only an approximate description. The ratio of $CaO/Si_2O$ is in between 1.2 and 2.3, which depends on water contain, aging time and temperature, and other factors. The high pH (pH=10-13) during hydration, in the presence of phosphate ions ($PO_4^{3-}$) increases the precipitation rate of the calcium phosphate, particularly hydroxyapatite, according to the reaction (A), which in turn decreases the overall alkalinity of hydration. Consequently, a process is created which both (i) decreases the alkalinity and CH content in the setting cement; and (ii) provides a strong and bio-active HAP phase which reinforces the composite.

In order to further remove the calcium hydroxide CH during setting of the cement, and thus further enhance its mechanical strength, additional phosphate may be introduced into the cement composition, which will continue to react with calcium hydroxide to form hydroxyapatite. If the calcium phosphate compound is calcium phosphate monobasic, the following dynamic chemical reaction takes place:

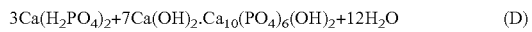

$$3Ca(H_2PO_4)_2 + 7Ca(OH)_2 \cdot Ca_{10}(PO_4)_6(OH)_2 + 12H_2O \quad (D)$$

The calcium hydroxide, produced during the hydration reaction of calcium silicates, reacts relatively rapidly with the phosphate compounds to produce the new compound, hydroxyapatite (HAP). Importantly, the same reaction (D) also provides water, which continues to react with the calcium silicates. The water supplied through reaction (D) is an important factor in controlling the hydration reaction speed, and thus setting time, hardening time, and the final mechanical strength of the composite biocement.

To further improve mechanical strength, silica nanoparticles may be introduced into the cement composition to react with remnant calcium hydroxide and thereby further decrease CH content and alkalinity of the cement.

The hydration rate of the calcium silicates (reactions B, C) increases as setting progresses, since the phosphate compounds in biocement react with calcium hydroxide to produce hydroxyapatite and water (reaction D), thus shifting the equilibrium. Therefore, the setting and hardening time of the biocement is shortened.

In the case of ordinary Portland cement (OPC) compositions, the hydration reactions of calcium silicates results in an increase of pH to over 12. In the cement composition of the present invention by contrast, the phosphate compounds react with the calcium hydroxide and thus neutralize the pH of the cement. The calcium hydroxide is therefore only the intermediate product of the hydration of calcium silicates in biocement of the present invention.

In ordinary Portland cement (OPC), the main strength providing compound is calcium silicate hydrate (C—S—H). C—S—H is an amorphous or poorly crystalline material which forms very small particles of submicron (less than 1 um) size. The calcium hydroxide CH, on the other hand, is a well-crystallized material with a definite stoichiometry, which occupies about 20-25% of the volume of OPC cement paste. The calcium hydroxide precipitates wherever free space is available and may completely engulf the cement grains. However, as noted above, calcium hydroxide is mechanically weak and it therefore greatly reduces the mechanical strength of the cement. In present invention, the calcium hydroxide is only an intermediate product, as it reacts with the phosphate compounds to produce the hydroxyapatite and water, according to reactions A and D.

In the set biocement of the present invention, the calcium silicate hydrate (C—S—H) interlocks with the hydroxyapatite, leading to in situ formation of a composite-like structure interspersed at a nanoscale level. The hydroxyapatite thus provides a reinforcement phase while the C—S—H forms the matrix of the composite structure. As a result, both phases contribute mechanical strength to the composite. By comparison with mineral trioxide aggregate (MTA) which, as noted above, is derived from ordinary Portland Cement, the mechanical strength and corrosion resistance of the material are significantly improved, because the weak phase calcium hydroxide of the former is replaced with high strength, chemically stable hydroxyapatite (HAP). The HAP has a compressive strength (>60 MPa) which is much higher than that of calcium hydroxide (<1 MPa). Moreover, hydroxyapatite ($Ca_{10}(PO_4)_6(OH)_2$) is one of the most biocompatible and bioactive ceramics because it is similar to the mineral constituents of natural human bone and teeth. Consequently, due to the relatively large content of HAP, the presently disclosed biocement of the present invention is not only bioactive and biocompatible, but also is osteoinductive and osteogenic (i.e., it encourages bone in-growth).

As a result, the cement of the present invention is especially suited for use in medical materials and devices, such as prostheses, implants, coatings, and other surgical procedures. The biocement is self-setting, injectable, and develops high strength cement, allowing it to be used for both weight and non-weight bearing applications. The cement can be deposited in a selected location in a patient's body and then allowed to cure to a solid therein. The cement resists disintegrative washout upon contact with blood, and injection into the wound is less stressful to the surrounding tissue because of being completely biocompatible with the physiological environment. Therefore examples of bio-medical applications for biocement of the present invention include, but not are limited to, orthopedic surgery, bone repair, bone reconstruction bone filling, bone fixation and combinations thereof, such as. for example, human and veterinary percutaneous vertebroplasty, craniomaxillofacial surgery, ridge augmentation, spinal fusion cage/implant, treatment of radial fractures, treatment of temporal mandibular, joint disorders, plastic surgery and cosmetic augmentation, bone graft substitution, scaffolding, drug delivery, and variations thereof. The biocement can also be used for dental applications, such as, for example, root canal filling, root canal sealing, root perforation repair, root resorption repair, root-end filling, retrofilling materials, pulp capping, apexification, and combinations thereof. The cement may also be used as a coating on devices, in particular medical implants. Another example includes use of the cement with drugs or proteins to address the specific medical problems, e.g.,. microspheres of biocement may be designed for targeted delivery of drugs, proteins, DNA, or other medically active species to areas of interest in the body.

The cement of the present invention can also be used make composite materials including specific secondary reinforcement phases, such as fibers, aggregates, bioglasses, bioceramics, polymers, and metals, in variety of morphological forms such as particles, fibers and loops for example.

c. Testing

FIGS. 1-6 illustrate the results of tests conducted using the cement compositions of the present invention, and in some instances also using control samples and/or prior materials (e.g., MTA/OPC) for comparison. These results will also be discussed in the following section with regard to the corresponding examples described therein.

FIG. 1 illustrates compressive strength of hydraulic cement as a function of calcium phosphate content. By incorporating 10-15 wt % calcium phosphates, the compressive strength of the set cement was significantly increased, from about 45 MPa to about 103 MPa (7 days setting time).

Figure 2:
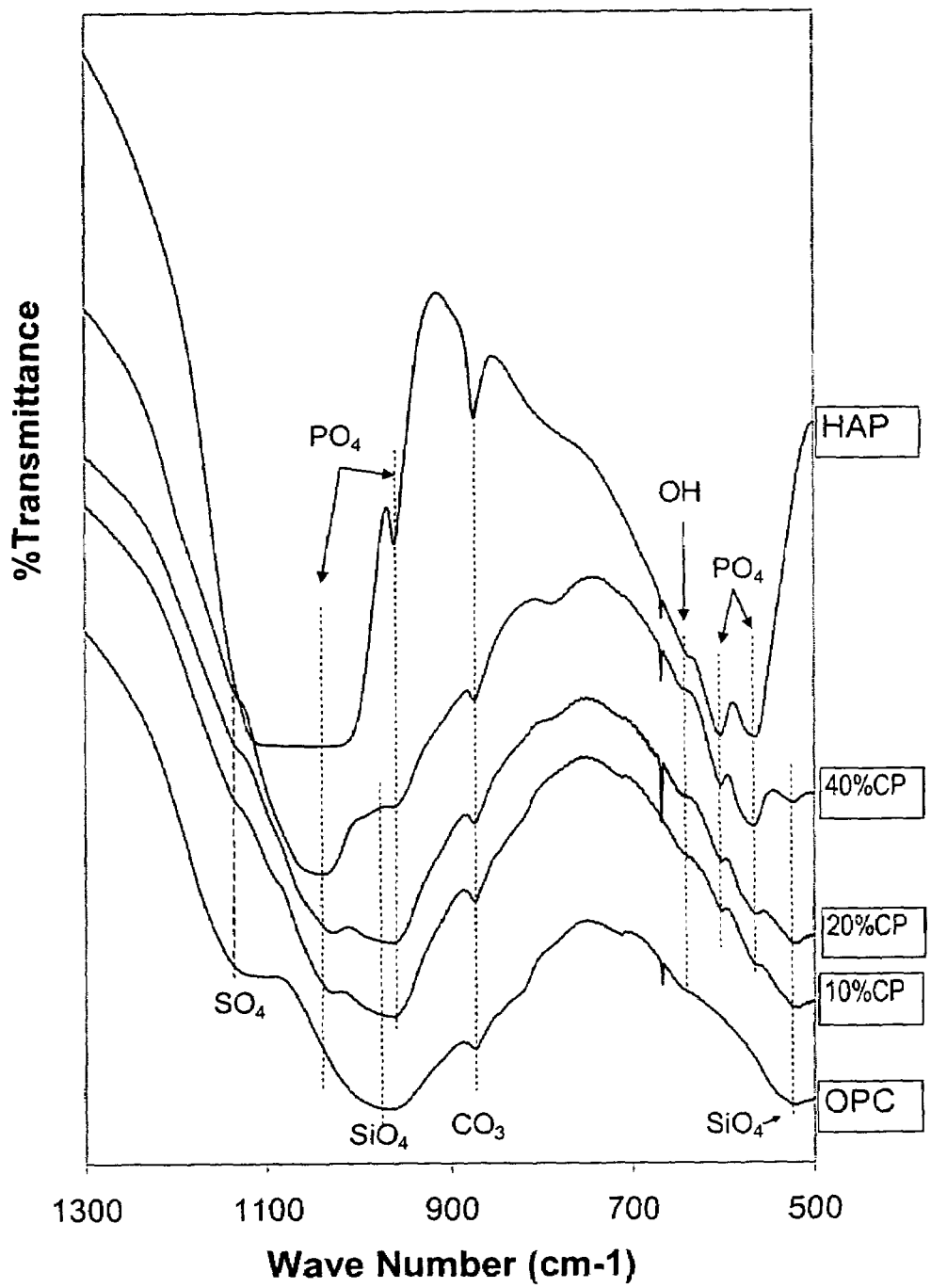
FIG. 2 is a graph illustrating FTIR spectra, of reference samples of Mineral Trioxide Aggregate (MTA, Portland Cement) and hydroxyapatite HAP, and of the hydraulic cement compositions of the present invention produced with differing amounts of calcium phosphate compounds.

FIG. 2 illustrates FTIR spectra of the reference samples of the Mineral Trioxide Aggregate (MTA, Portland Cement) and the hydroxyapatite HAP, and the novel biocement compositions of the present invention produced with differing amounts of calcium phosphate compounds.

FTIR spectra provide essential features of the cements. There are three main regions related to the vibration frequencies of $SO_4$, $SiO_4$, and $CO_3$ groups in wave number ranges 500-1300 $cm^{-1}$. For the MTA samples, the sulfate absorption bands (i.e. the S—O stretching bands) at 1150-1100 cm in hydrated Portland cement are shown as a shoulder band. The bands at 960 $cm^{-1}$ and 520 $cm^{-1}$ are contributed by the Si—O asymmetric stretching and the Si—O out-of-plane bending vibration of $SiO_4$ group of calcium silicate hydrate gel. Another band at 870 $cm^{-1}$ is contributed by the vibration of $CO_3$ group [refer also to the Mollah et al, "*A Fourier transform infrared spectroscopic investigation of the earlyhydration of Portland cement and the influence of sodium lignosulfonate*" Cement and Concrete Research 30 (2000) 267-273].

For the hydroxyapatite (HAP) (see FIG. 2) reference sample, the absorption spectrum has three main regions related to the vibration frequencies of the $OH^-$, $PO_4^{3-}$ and $CO_3^{2-}$ ions [Vaidya, et al, *Pressure-induced crystalline to amorphous transition in hydroxylapatite, J. Mater. Sci.*, 32 (1997) 3213-3217]. The absorption of the internal stretching of OH in hydroxyapatite is located at 630 $cm^{-1}$. The vibrations of the phosphate ions are an asymmetric stretch (1100-1028 $cm^{-1}$), a degenerate symmetric stretch (960 $cm^{-1}$), and a double degenerate asymmetric bend (600 $cm^{-1}$ and 560 $cm^{-1}$). The $CO_3^{2-}$ has vibration band at 870 $cm^{-1}$. This is a typical amorphous or poor crystallinity structure hydroxyapatite.

By comparison with MTA, the frequencies of bands of vibration and liberation modes of various functional groups representative of hydroxyapatite appear on FTIR spectra of the cement of the present invention when including 10 wt % calcium phosphate compounds. As can be seen in FIG. 2, the intensity of absorption bands increases with increasing content of calcium phosphate compounds. This indicates formation of hydroxyapatite in the cement composition of the present invention.

Figure 3A:
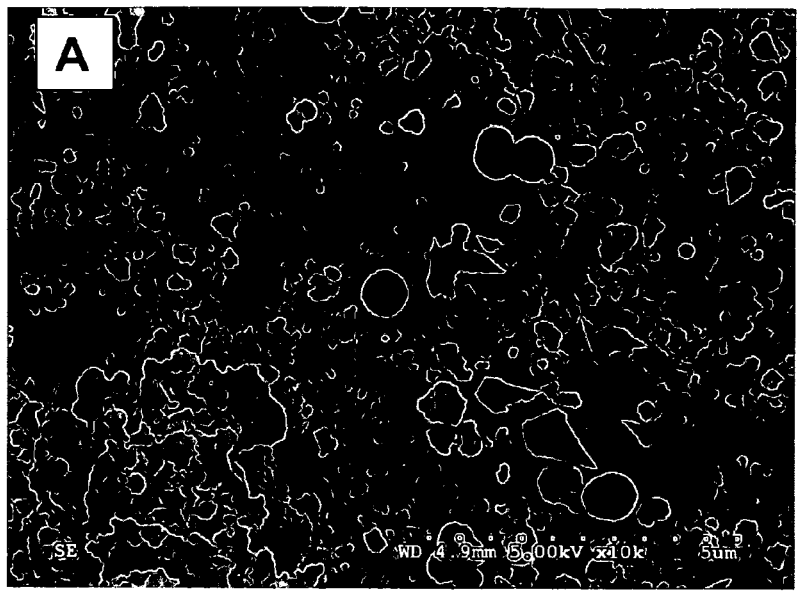
FIG. 3 is an electron microscope scan illustrating the results of a bioactivity test conducted for (A) MTA and (B) the hydraulic cement of the present invention containing 20% of calcium phosphates.
Figure 3B:
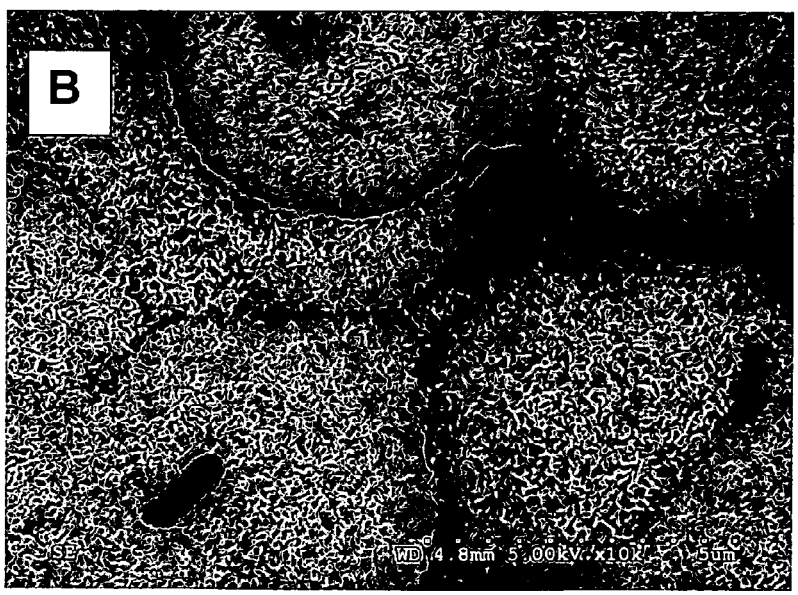
Figures 4A, 4B:
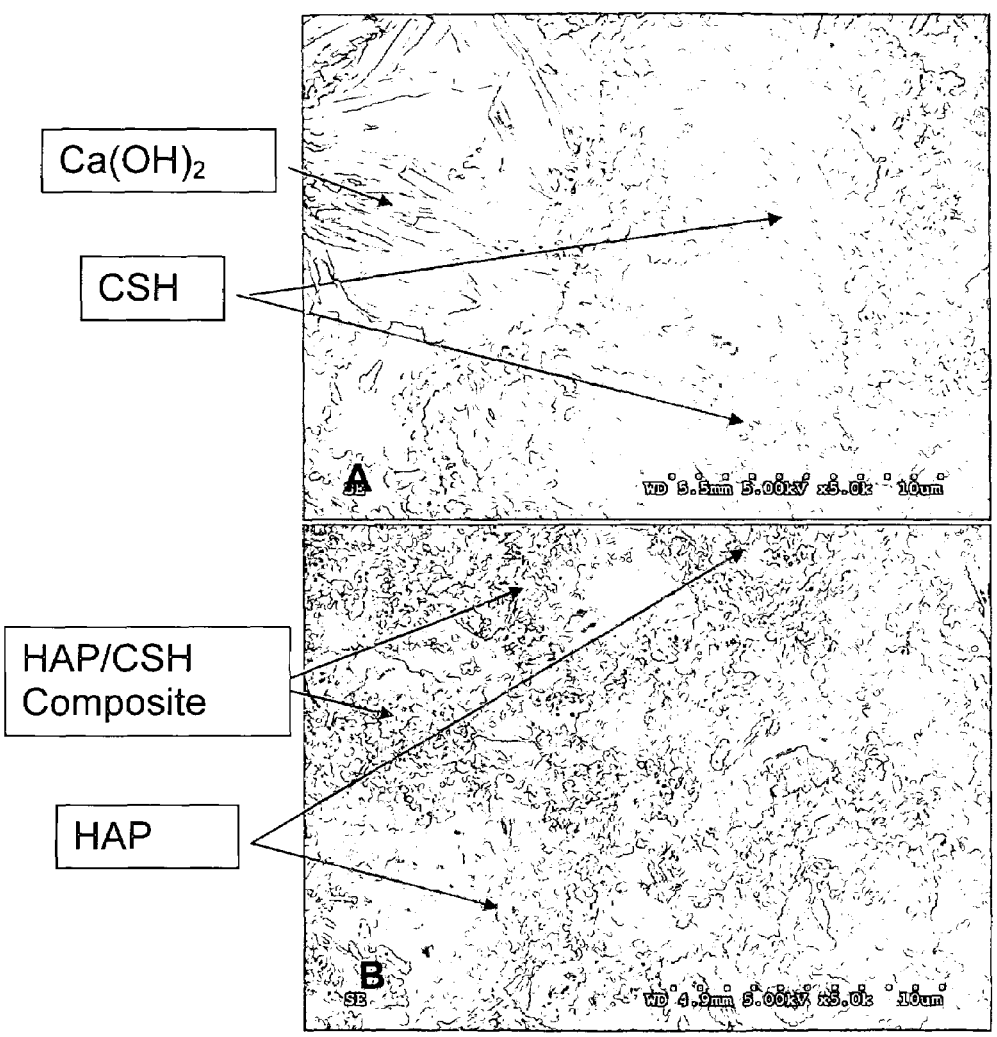
FIG. 4 is an electron microscope scan illustrating the microstructures of fracture surfaces of (A) MTA and (B) the hydraulic cement of the present invention, at 2000 magnification.

FIG. 3 illustrates the results of bioactivity tests preformed for (A) MTA, and for (B) the hydraulic cement of the present invention with 20% of calcium phosphate. In accordance with accepted methods of bioactivity testing, all samples were immersed in SBF (Simulated Body Fluid) solution at 37 C for 10 days, after which the samples were washed with distilled water and dried for SEM observations. No hydroxyapatite formation was observed on surface of MTA by SEM, indicating that MTA is not bioactive. However, a typical hydroxyapatite structure layer formed on the surface of the cement of the present invention, indicating that the cement has good bioactivity.

FIG. 4 illustrates the microstructures of fracture surfaces of MTA (FIG. 4 (A)) and the hydraulic cement of the present invention (FIG. 4 (B)), at 2000× magnification. FIG. 4 (A) clearly shows relatively large $Ca(OH)_2$ crystals in the MTA, which as noted above is one of the hydration products of calcium silicates. The calcium hydroxide does not form homogenous crystals in the cement paste, but rather grows into the free space, such as pores and voids. By contrast, large $Ca(OH)_2$ crystals are absent in the cement of the present invention, as illustrated in FIG. 4 (B); instead, a composite of HAP/C—S—H can be observed on the surface. The in-situ formation of HAP/C—S—H composite was confirmed by EDX analysis.

Figure 5A:
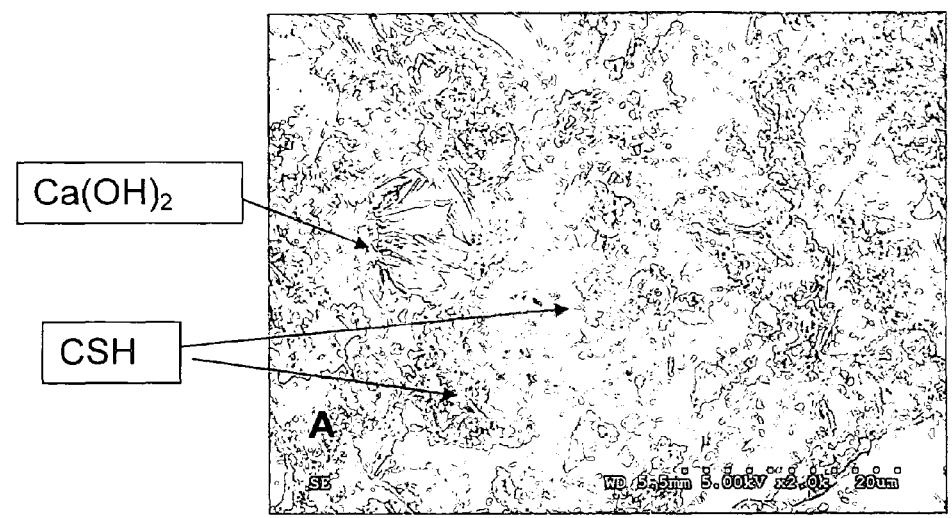
FIG. 5 is an electron microscope scan illustrating the microstructures of the fracture surfaces of (A) MTA and (B) the hydraulic biocement of the present invention at 5000× magnification.
Figure 5B:
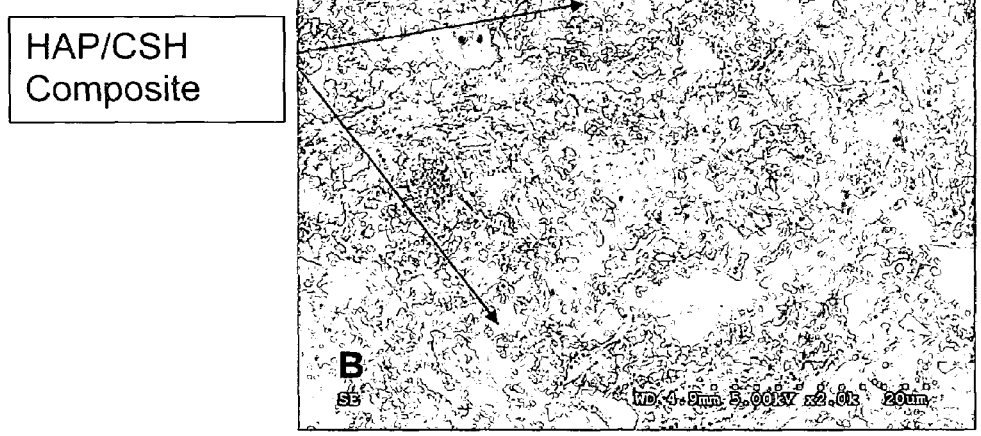

FIG. 5 in turn, illustrates the microstructures of the fracture surfaces of MTA (FIG. 5A) and the biocement of the present invention (FIG. 5(B)) at 5000× magnification. FIG. 5 (A) clearly shows the crystal structure of $Ca(OH)_2$. The pure HAP phase and HAP/CSH composite are observed in the biocement samples shown in FIG. 5 (B), which was confirmed by EDX analysis.

Figure 6:
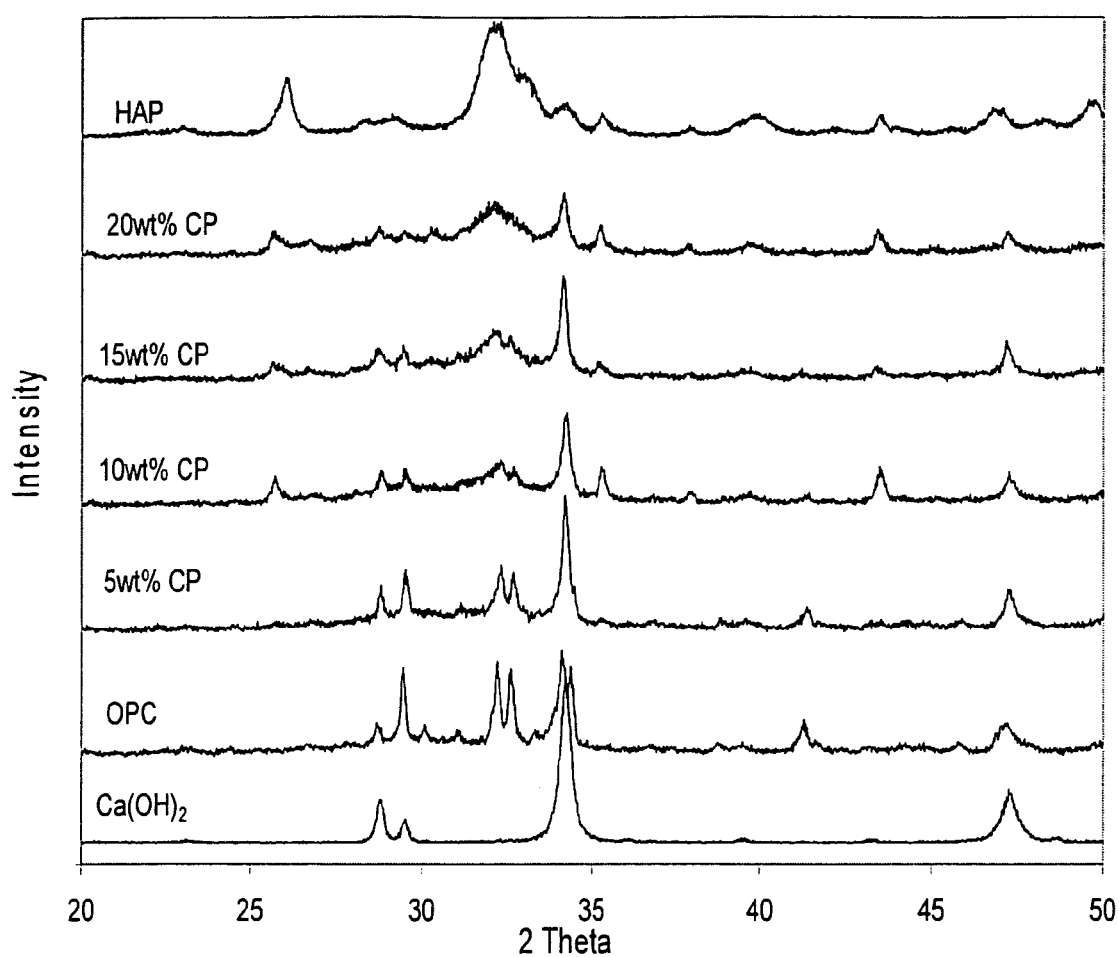
FIG. 6 is a graph of X-ray diffraction patterns, for the hydraulic cement of the present invention containing differing percentages of calcium phosphate, together with reference plots for hydroxyapatite (HAP) ordinary Portland cement (OPC), and pure calcium hydroxide ($Ca(OH)_2$).

FIG. 6 compares X-ray diffraction patterns for Mineral Trioxide Aggregate (labeled OPC), and for the hydraulic cement of the present invention with differing amounts of calcium phosphate. Additionally, for reference, the bottom pattern is from pure calcium hydroxide, and the top pattern is from pure amorphous/poor crystallinity hydroxyapatite (i.e. the type of HAP forming during the dissolution-precipitation setting reaction). As can be seen, the hydroxyapatite diffraction peak at 32.3 degree of 2-Theta angle starts to appear with 10 wt % CP. The relative intensity of the X-ray diffraction peaks of calcium hydroxide decrease simultaneously with the increase of the calcium phosphate content in the calcium-silicate cement (i.e. observe the decreasing of $Ca(OH)_2$ peak intensity at about 47.5 Two-Theta). This X-ray diffraction pattern indicates that the calcium phosphate additive dissolves in water, reacts with calcium hydroxide (which is the hydration product of calcium silicates) and subsequently precipitates the hydroxyapatite.

EXAMPLES

Example 1

Preparation of Novel High Strength Biocement for Orthopedic Applications

In this example the phosphate silicate cement was prepared synthetically using well defined, substantially pure chemicals (as opposed to the poorly defined minerals utilized for preparation of the typical commercial Portland cements). The raw materials used were colloidal silica (50 wt % Ludox, from 3M company) for the $SiO_2$ component, calcium hydroxide (99.9%, Sigma-Aldrich) for the CaO component, tetracalcium phosphate ($Ca_4(PO_4)_2O$), and dicalcium phosphate anhydrate ($CaHPO_4.H_2O$) (Fisher). The designed composition was 65 wt % tricalcium silicate, 20 wt % dicalcium silicate, 10 wt % tetracalcium phosphate, and 5 wt % dicalcium phosphate.

A 200 g cement batch was prepared by mixing 96.32 g of colloidal silica, 160.98 g calcium hydroxide, and 300 g distilled water in a ceramic jar, followed by ball milling for 24 hours. The slurry of this mixture was dried by using a spray dryer, and then fired in high temperature furnace at 1550° C. for 1 hour to form tricalcium silicate and dicalcium silicate, after which it was naturally cooled to room temperature. The resulting cement clinker was ground to −325 sieve particle size (<45 um particle size), with an average particle size of about 10 um. 11.25 g of dicalcium phosphate anhydrate was dried in the furnace at 140° C. for 24 hours and then mixed with 20 g of the tetracalcium phosphate and with the fired cement powder (168 grams) in alcohol solution, allowed by ball milling for 24 hours. The resulting slurry was spray dried. The average particle size of the cement powder was about 10 um.

The setting time of the cement was about 4 hours. The average compressive strength after 7-day incubation at 37° C. and 100% humidity was 104 MPa, with a standard deviation of 7 MPa. The control samples of the cement without the addition of phosphates, and set under identical conditions, had an average compressive strength of 45. MPa, with a standard deviation of 5 MPa.

Example 2

Preparation and Properties of Phospho-Silicate Hydraulic Cement by Sol-Gel Process This example utilized a sol-gel process to prepare high-purity, aluminum-free biocement. Tetraethylorthosilicate (TEOS), $Ca(NO_3)_2 \cdot 4H_2O$, triethyl phosphate (TEP) were used in the sol-gel method. $Ca(NO3)_2 \cdot 4H_2O$ was dissolved in 1M $HNO_3$ solution and TEOS was added to the solution with vigorous stirring to obtain a nominal composition of 70 mol % CaO-30% $SiO_2$. After 10-15 min of hydrolysis under stirring, a homogenous sol was obtained. The sol precursor was sealed in a container, where the precursor was allowed to gel for 1 day at room temperature and aged for another day at 70° C. The dry gel powder was obtained by heating the templated gel at 600° C. in air for 1 hour (heating rate: 2° C./min). The dry powder was fired at 1400° C. for 2 hrs. The crystalline product was analyzed by X-ray diffraction (XRD). The results of XRD indicated that the product contained only the phases of tricalcium silicate and dicalcium silicate.

The biocement was obtained by mixing 75 wt % of the sintered powder with 15 wt % calcium phosphate mono-basic and 10 wt % dicalcium phosphate in planetary ball mill for 10 min. The average particle size of the cement powder was about 2 um. The properties of the resulting set biocement were evaluated as follows: compressive strength of 72 MPa and setting time of 1 hour.

The set samples of the biocement were submerged into Simulated Body Fluid (SBF) solution at 37° C. for 7 days for testing bioactivity of the biocement. The surface morphology of the cement particles was examined by SEM, and EDX analysis was performed for elemental composition. The results show that a typical (for a highly bioactive material) hydroxyapatite structure film was deposited on the surface of biocement, as shown in FIG. 3. The film was confirmed to be hydroxyapatite by EDX analysis (for elemental composition) and XRD (for phase composition).

Example 3

Effect of Calcium Phosphate on the Properties and Microstructure of Biocement In this example, biocement was prepared in the same manner as described in Example 1. The setting time of was about 1 hour to 4 hours, for a water/cement ratio of 0.25. The average compressive strength after 7-days incubation at 37° C. and 100% humidity was 104 MPa, with the standard deviation of 7 MPa, as shown in FIG. 1.

The X-ray diffraction pattern provided in FIG. 6 indicates that the set cement contained about 15% HAP, and about 8% $Ca(OH)_2$. This is compared with the characteristics of the control samples without calcium phosphate material, hydrated under identical conditions as the above samples of biocement. The average compressive strength of calcium silicate control cement was 45 MPa, with a standard deviation of 5 MPa, again referring to FIG. 1. The X-ray diffraction pattern provided in FIG. 6 indicates that the set control sample contained no HAP, and about 20% of $Ca(OH)_2$. The scanning electron microscope microstructures shown in FIGS. 4A and 5A (calcium silicates) and FIGS. 4B and 5B (biocement) clearly indicate the composite character and decreased CH content of the biocement of the present invention.

Example 4

Preparation of Novel High Strength White Biocements for Dental Applications

The following procedure was used to prepare high-strength bioactive and biocompatible biocement for dental applications.

The raw materials used were colloidal silica (50 wt % Ludox, 3M) for the $SiO_2$, calcium hydroxide (99.9%, Sigma-Aldrich) for the CaO, iron oxide ($Fe_2O_3$, 99% Fisher), calcium sulfate dehydrate ($CaSO_4 \cdot H_2O$, 99%, Fisher), $Ca(OH)_2$, and monocalcium phosphate ($Ca(H_2PO_4)_2$, 99%, sigma). The designed composition was 62 wt % tricalcium silicate (3CaO·$SiO_2$), 18 wt % dicalcium silicate (2CaO·$SiO_2$), 4 wt % calcium sulfate dehydrate ($CaSO_4 \cdot 2H_2O$), 4 wt % calcium oxide, and 12 wt % monocalcium phosphate ($Ca(H_2PO_4)_2$). A 200 g batch was prepared by mixing in 300 g distilled water in a plastic jar, followed by zriconia ball milling for 24 hours. The slurry mixture was dried using a spray dryer, and then fired in a high a temperature furnace at 1550° C. for 1 hour. It was then naturally cooled to room temperature, followed by grinding to about 10 um average particle size. 20 g of monocalcium phosphate, 8 g of calcium hydroxide, and 8 g of calcium sulfate dehydrate were mixed with the fired cement powder in alcohol solution by ball milling for 4 hours. The slurry was dried by using spray a dryer.

The setting time of the cement prepared as described was around 2 hours, for a water/cement ratio of 0.21. The compressive strength following a 7-day incubation at 37° C. and 100% humidity was 110 MPa, with a standard deviation of 7 MPa. Control samples of the cement, without the addition of phosphates and set under identical conditions, had an average compressive strength of 48 MPa, with a standard deviation of 4 MPa. The X-ray diffraction pattern provided in FIG. 6 indicates that the set biocement contained about 15% HAP.

This biocement paste was injectable, gray in color, and suitable for dental applications, such as a root-end filling material, retrofilling material, pulp capping, apexification, and the sealing of perforations. To make a white color biocement for dental applications requiring color control (e.g. for cosmetic reasons), all of the preparation steps described above were repeated exactly, except that the iron oxide was excluded from the composition. The properties of the white variant of the biocement were essentially the same as the properties of the gray variant.

Example 5

In Vitro Testing of Bioactivity

This example compared the bioactivity of prior mineral trioxide aggregates (MTA) to a cement in accordance with the present invention having 10% calcium phosphate.

The paste samples were prepared by mixing the cement powder with distilled water at the water/cement ratio of w/c=0.25. The cement paste was filled into a cylinder mold having a 1-inch diameter and 2-inch height. The samples were incubated at 100% humidity and the procedure described by Li, et at, [*Apatite formation induced by silica gel in a simulated body fluid. J Am Ceram Soc* 75 (1992), pp. 2094-2097] was followed without use of any organic species, and with pH adjusted to 7.4 with 7.5% $NaHCO_3$ solution.

All samples were immersed in SBF solution at 37C for 7 days. The samples were then washed with distilled water and dried for SEM observations, which are illustrated in FIGS. 3, 4 and 5. No hydroxyapatite formation was observed on the surface of the MTA by SEM, indicating that MTA is not bioactive. However, a typical hydroxyapatite structure layer was observed to be forming on the surface of the biocement of the present invention, indicating that the cement has good bioactivity, osteoinductivity, and osteogenicity.

Example 6

Biocement Composition with Radio-Opaque Component for Dental Applications

This example illustrates procedure for making a dental cement that incorporates a radio-opaque material.

The fired cement powders were prepared as described in Example 3. Zirconia ($ZrO_2$, Zircoa, USA) was chosen as the radio-opaque material for dental application, because zirconia is biocompatible and is used for orthopedic implant devices. 80 g of the biocement powder and 20 g of zirconia powder were mixed in a powder mixer for 20 min.

X-ray tests showed clear visibility of the modified biocement, demonstrating that the dental cement with zirconia radio-opaque is suitable for dental applications.

Example 7

Effect of Silicate Nanoparticles on Biocement Properties

This example showed that nanoparticle silicates can be used as beneficial additives in the biocement of the present invention. Suitable silicate nanoparticle material can be purchased from commercial suppliers, such Lodux colloidal silica. Also, silica nanoparticles can easily be synthesized through a sol-gel process, e.g. decomposition of TEOS.

The biocement powder was prepared as described in Example 2 above. 20 wt % colloidal silicate (Ludox) was mixed with biocement powders to form the cement paste. The results were a compressive strength of 110 MPa, and a setting time of 40 min.

The set samples were immersed in SBF solution at 37° C. for 3 days to test bioactivity. The surface morphologies were examined by SEM and EDX analysis of elements. The SEM results showed that a characteristic hydroxyapatite structure film was deposited on the surface of biocement. The film was confirmed to be hydroxyapatite by EDX and XRD analysis.

It is to be recognized that various alterations, modifications, and/or additions may be introduced into the constructions and arrangements of parts described above without departing from the spirit or ambit of the present invention as defined by the appended claims.

What is claimed is:

1. A bio-active and biocompatible hydraulic cement composition for medical and dental applications that reacts with water at a substantially neutral pH, said hydraulic cement composition comprising:
   at least one calcium silicate compound that produces calcium silicate hydrate-gel and calcium hydroxide during hydration when water is added to said composition at near neutral pH, said at least one calcium silicate compound being selected from the group consisting of:
   di-calcium silicate;
   tri-calcium silicate;
   tetra-calcium silicate; and
   combinations thereof; and
   calcium phosphate monobasic that reacts with said calcium hydroxide that is produced by hydration of said at least one calcium silicate compound to produce hydroxyapatite in-situ during setting of said composition;
   said hydraulic cement composition being substantially free of both aluminum and magnesium.

2. The cement composition of claim 1, comprising said calcium phosphate monobasic
   in an amount sufficient to react a major portion of said calcium hydroxide produced by hydration of said at least one calcium silicate compound.

3. The cement composition of claim 1, wherein said at least one calcium silicate compound comprises:
   at least one calcium silicate compound in an amount sufficient to hydrate with water to form a gel-like calcium silicate and calcium hydroxide mixture.

4. The cement composition of claim 3, comprising said calcium phosphate monobasic in an amount sufficient to react a major portion of calcium hydroxide produced during hydration of said to form in-situ hydroxyapatite or other calcium phosphates that precipitates within said gel-like mixture.

5. The cement composition of claim 1, comprising said calcium phosphate monobasic in an amount in the range from about 1% to about 70% by weight of said cement composition.

6. The composition of claim 5, comprising said calcium phosphate monobasic in an amount within the range from about 5% to about 30% by weight of said cement composition.

7. The cement composition of claim 1, comprising said at least one calcium silicate compound in an amount in a range from about 30% to about 99% by weight of said cement composition.

8. The cement composition of claim 6, comprising said calcium silicate compound in an amount within the range from about 40% to about 80% by weight of said cement composition.

9. The cement composition of claim 1, further comprising:
   at least one ancillary compound which in total comprise less than about 30% by weight of said cement composition.

10. The cement composition of claim 9, wherein said at least one ancillary compounds is selected from the group consisting of:
    silicon dioxide;
    calcium sulphate;
    calcium sulphate dihydrate;
    metal oxide compounds; and
    combinations thereof.

11. The cement composition of claim 1, further comprising:
    at least one radiopaque substance.

12. The cement composition of claim 11, wherein said radiopaque substance is selected from the group consisting of:
    heavy metals;
    oxides of heavy metals;
    salts of heavy metals; and
    combinations thereof.

13. The cement composition of claim 12, wherein said radiopaque substance is selected from the group consisting of:
    gold;
    silver;
    barium;
    bismuth;

tantalum;
barium sulphate;
bismuth oxide;
tantalum oxide;
zirconium oxide; and
combinations thereof.

14. The cement composition of claim 11, comprising said at least one radiopaque substance in an amount within the range from about 3% to about 50% by weight of said cement composition.

15. The cement composition of claim 14, comprising said at least one radiopaque substance in an amount within the range from about 10% to about 40% by weight of said cement composition.

16. A method for treatment of medical or dental conditions using a hydraulic cement that reacts with water at a substantially neutral pH, said method comprising the steps of:
    providing a bioactive and biocompatible hydraulic cement comprising:
        water at a substantially neutral pH;
        at least one calcium silicate compound that produces calcium silicate hydrate gel and calcium hydroxide during hydration with said water, said at least one calcium silicate compound being selected the group consisting of:
        di-calcium silicate;
        tri-calcium silicate;
        tetra-calcium silicate; and
        combinations thereof; and
        calcium phosphate monobasic, that reacts with said calcium hydroxide that is produced by hydration of said at least one calcium silicate compound, to produce in-situ at least one calcium phosphate compound during setting of said cement;
        said hydraulic cement being substantially free of both aluminum and magnesium;
    depositing said hydraulic cement in a selected location in the body of a patient; and
    allowing said hydraulic cement to cure to solid in said selected location in the body of said patient.

17. The method of claim 16, wherein the steps of depositing said hydraulic cement in a selected location in the body of a patient comprises depositing said hydraulic cement as a dental treatment selected from the group consisting of:
    root canal filling;
    root canal sealing;
    pulp capping;
    apexification;
    root perforation repair;
    root resorption repair;
    root end filling; and
    combinations thereof.

18. The method of claim 16, wherein the steps of depositing said hydraulic cement in a selected location in the body of a patient comprises depositing said hydraulic cement as a medical treatment selected from the group consisting of:
    orthopedic surgery;
    bone repair;
    bone reconstruction;
    bone filling;
    bone fixation; and
    combinations thereof.

\* \* \* \* \*